US011339105B2

(12) United States Patent
Luo et al.

(10) Patent No.: US 11,339,105 B2
(45) Date of Patent: May 24, 2022

(54) METHODS FOR OPERATING DEHYDROGENATION PROCESSES DURING NON-NORMAL OPERATING CONDITIONS

(71) Applicant: Dow Global Technologies LLC, Midland, MI (US)

(72) Inventors: Lin Luo, Sugar Land, TX (US); Matthew T. Pretz, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 17/272,741

(22) PCT Filed: Aug. 15, 2019

(86) PCT No.: PCT/US2019/046598
§ 371 (c)(1),
(2) Date: Mar. 2, 2021

(87) PCT Pub. No.: WO2020/060700
PCT Pub. Date: Mar. 26, 2020

(65) Prior Publication Data
US 2021/0371357 A1 Dec. 2, 2021

Related U.S. Application Data

(60) Provisional application No. 62/732,276, filed on Sep. 17, 2018.

(51) Int. Cl.
C07C 5/48 (2006.01)
B01J 38/12 (2006.01)
(Continued)

(52) U.S. Cl.
CPC .............. *C07C 5/48* (2013.01); *B01J 8/0025* (2013.01); *B01J 8/1818* (2013.01); *B01J 8/26* (2013.01);
(Continued)

(58) Field of Classification Search
CPC ... C07C 5/48; C07C 2523/08; C07C 2523/42; C07C 11/02; B01J 8/0025; B01J 8/1818;
(Continued)

(56) References Cited

U.S. PATENT DOCUMENTS 5,458,920 A   10/1995  Yezrielev et al.
7,951,873 B2   5/2011  Best et al.
(Continued)

FOREIGN PATENT DOCUMENTS

WO   2017003884 A1   1/2017

OTHER PUBLICATIONS

International Search Report and Written Opinion pertaining to PCT/US2019/046598, dated Nov. 18, 2019.
(Continued)

*Primary Examiner* — Philip Y Louie
*Assistant Examiner* — Jason Y Chong
(74) *Attorney, Agent, or Firm* — Dinsmore & Shohl LLP

(57) ABSTRACT

According to one or more embodiments disclosed herein, methods for operating dehydrogenation processes during non-normal operating conditions, such as at start-up, shut-down, system recycle, or unit trip, are described. The methods may include contacting a feed stream with a catalyst in a reactor portion of a reactor system to form a reactor effluent stream, separating at least a portion of the reactor effluent stream from the catalyst, passing the catalyst to a catalyst processing portion and processing the catalyst, wherein processing the catalyst comprises contacting the catalyst with oxygen, passing the catalyst from the process-
(Continued)

ing portion to the reactor portion, wherein the catalyst exiting the processing portion comprises at least 0.001 wt. % oxygen, and contacting the catalyst with supplemental hydrogen, the contacting removing at least a portion of the oxygen from the catalyst by a combustion reaction.

18 Claims, 4 Drawing Sheets

(51) Int. Cl.
    *B01J 8/00*         (2006.01)
    *B01J 8/18*         (2006.01)
    *B01J 8/26*         (2006.01)

(52) U.S. Cl.
    CPC ............... *B01J 2208/00663* (2013.01); *B01J 2208/00752* (2013.01); *C07C 2523/08* (2013.01); *C07C 2523/42* (2013.01)

(58) Field of Classification Search
    CPC ............... B01J 8/26; B01J 2208/00663; B01J 2208/00752
    See application file for complete search history.

(56) References Cited

U.S. PATENT DOCUMENTS

| | | |
|---|---|---|
| 9,815,040 B2 | 11/2017 | Pretz et al. |
| 9,827,543 B2 | 11/2017 | Pretz et al. |
| 9,834,496 B2 | 12/2017 | Pretz et al. |
| 10,688,477 B2 | 6/2020 | Pretz et al. |
| 2008/0194891 A1* | 8/2008 | Pretz ............... C07C 5/3332 585/252 |
| 2014/0124408 A1 | 5/2014 | Zeng et al. |
| 2014/0249339 A1* | 9/2014 | Simanzhenkov ...... B01J 23/002 585/252 |
| 2014/0316181 A1* | 10/2014 | Averlant ............... C07C 7/163 585/850 |

OTHER PUBLICATIONS

Examination Report pertaining to corresponding Gulf Cooperation Council Patent Application No. GC 2019-38296, dated Nov. 24, 2020.
Examination Report pertaining to corresponding Gulf Cooperation Council Patent Application No. GC 2019-38296, dated Aug. 30, 2020.
Mohundro, Edgar L., "Overview on C2 and C3 Selective Hydrogenation in Ethylene Plants", 15th Ethylene Produces Conference, 2003, AICHE Spring National Meeting, New Orleans, LA.
U.S. Office Action dated Mar. 31, 2022 pertaining to U.S. Appl. No. 17/269,750, filed Feb. 19, 2021, 22 pages.
Vistamaxx Material Safety Data Sheet, Ex xonMobil, 2002.

\* cited by examiner

METHODS FOR OPERATING DEHYDROGENATION PROCESSES DURING NON-NORMAL OPERATING CONDITIONS

CROSS-REFERENCE TO RELATED APPLICATIONS

This application is a National Stage Entry under 35 U.S.C. § 371 of International Patent Application No. PCT/US2019/046598, filed Aug. 15, 2019, which claims priority to U.S. Provisional Patent Application No. 62/732,276 filed on Sep. 17, 2018, the entire disclosures of which are hereby incorporated by reference.

BACKGROUND

Field

The present disclosure generally relates to chemical processing systems and the operation thereof and, more specifically, to dehydrogenation processes.

Technical Background

Dehydrogenation reactions utilizing, for example, fluidized catalysts may be useful in manufacturing olefins from hydrocarbon feeds. Such processes may operate at high temperatures (e.g., greater than 550° C., such as from about 580° C. to about 750° C.) conducive to the catalyzed dehydrogenation reaction. Under such normal operating conditions, a hydrocarbon is dehydrogenated, forming at least hydrogen and olefins. Such processes may be operated for long periods of time under relatively steady state operation.

However, during non-normal processing conditions such as at process start-up, shut-down, system recycle, and in the event of a unit trip, temperatures in the dehydrogenation reactor unit may be substantially lower than under normal operating conditions, and reactions in the system may be affected by the lower temperature. Such variation in the reactions may create unsafe operating conditions, and methods which account for the non-normal operating conditions are needed.

SUMMARY

It has been found that in dehydrogenation reactor systems such as those described herein, non-normal operating conditions at lower temperatures may lead to an excess amount of oxygen in reaction products and building up within the system. For example, free oxygen may be present in the dehydrogenation catalyst following cyclic regeneration and, under normal operating conditions, may react with hydrocarbons in the dehydrogenation reactor, thus removing free oxygen from the system. However, at lower temperatures, such oxygen may fail to react with the present hydrocarbons and remain as a system product. In other situations, no hydrocarbons may be present to react with the free oxygen, such as when nitrogen or other inert gas is circulated through the reactor system to fluidize the catalyst. Such free oxygen may cause unsafe operating conditions in the dehydrogenation reactor system, downstream separation units, and/or other reactor units which are in any way connected with the dehydrogenation reactor system. During start-up, shutdown, out-of-specification product event, or other planned or unplanned event, the reactor product may be recycled directly or indirectly to the reactor which can cause a build-up of oxygen. By way of example, a build-up of oxygen in the dehydrogenation system, sometimes referred to as free oxygen herein, may have the potential for highly exothermic reactions (e.g., explosions) which is an obvious safety concern.

According to one or more embodiments described herein, the problem of free oxygen in the dehydrogenation system in non-normal operating conditions may be addressed by adding supplemental hydrogen to the dehydrogenation system. The presence of supplemental hydrogen (i.e., hydrogen not formed in the dehydrogenation reaction) may allow for combustion of the free oxygen carried by the catalyst or released from the catalyst. Under such non-normal conditions, hydrogen may not be produced by the dehydrogenation of the feed hydrocarbons in an amount sufficient to react with the free oxygen, and the oxygen may not be otherwise reacted with hydrocarbons due to the low temperature. Additionally, in certain other non-normal conditions, such as start-up and shutdown for example, nitrogen or other inert gases may be circulated in the reactor system to fluidize the catalyst in the absence of a hydrocarbon feed. The presently disclosed embodiments allow for the oxygen buildup to be mitigated or even completely corrected during low temperature reactor conditions during non-normal operation, such as start-up, shut-down, system recycle, or unit trip.

According to one embodiment presently described, a method for operating a dehydrogenation process during non-normal operating conditions (e.g., start-up, shutdown, system recycle, or unit trip) may include contacting a feed stream with a catalyst in a reactor portion of a reactor system to form a reactor effluent stream, separating at least a portion of the reactor effluent stream from the catalyst, passing the catalyst to a catalyst processing portion and processing the catalyst, wherein processing the catalyst comprises contacting the catalyst with an oxygen-containing stream (e.g., air or other oxygen-containing stream), passing the catalyst from the processing portion to the reactor portion, wherein the catalyst exiting the processing portion comprises at least 0.001 wt. % oxygen, and contacting the catalyst with supplemental hydrogen, the contacting removing at least a portion of the oxygen from the catalyst by a combustion reaction. The temperature or the molar ratio of hydrocarbon to oxygen in the reactor portion is less than a temperature or molar ratio of hydrocarbon to oxygen needed for 50% of the oxygen to react with one or more hydrocarbons present in the reactor portion.

According to another embodiment presently described, a method for operating a dehydrogenation process during non-normal operating conditions (e.g., start-up, shut-down, system recycle, or unit trip) may include contacting a feed stream with a catalyst in a reactor portion of a reactor system to form a reactor effluent stream, separating at least a portion of the reactor effluent stream from the catalyst, passing the catalyst to a catalyst processing portion and processing the catalyst, wherein processing the catalyst comprises contacting the catalyst with an oxygen-containing stream (e.g., air or other oxygen-containing gas), passing the catalyst from the processing portion to the reactor portion, wherein the catalyst exiting the processing portion comprises at least 0.001 wt. % oxygen, and contacting the catalyst with supplemental hydrogen, the contacting removing at least a portion of the oxygen from the catalyst by a combustion reaction. The temperature in the reactor portion may be less than 550° C.

According to another embodiment presently described, a method for operating a dehydrogenation process during non-normal operating conditions (e.g., start-up, shutdown, system recycle, or unit trip) may include contacting a feed stream with a catalyst in a reactor portion of a reactor system to form a reactor effluent stream, separating at least a portion of the reactor effluent stream from the catalyst, passing the catalyst to a catalyst processing portion and processing the catalyst, wherein processing the catalyst comprises contacting the catalyst with an oxygen-containing stream (e.g., air or other oxygen-containing stream), passing the catalyst from the processing portion to the reactor portion, wherein the catalyst exiting the processing portion comprises at least 0.001 wt. % oxygen, and contacting the catalyst with supplemental hydrogen, the contacting removing at least a portion of the oxygen from the catalyst by a combustion reaction. The temperature in the reactor portion may be less than a temperature needed for 50% of the oxygen to react with one or more hydrocarbons present in the reactor portion.

According to yet another embodiment presently disclosed, a method for operating a dehydrogenation processes during non-normal operating conditions (e.g., start-up, shut-down, system recycle, or unit trip) may include contacting a feed stream with a catalyst in a reactor portion of a reactor system to form a reactor effluent stream, separating at least a portion of the reactor effluent stream from the catalyst, passing the catalyst to a catalyst processing portion and processing the catalyst, wherein processing the catalyst comprises contacting the catalyst with an oxygen-containing stream (e.g., air or other oxygen-containing stream), passing the catalyst from the processing portion to the reactor portion, wherein the catalyst exiting the processing portion comprises at least 0.001 wt. % oxygen, and contacting the catalyst with supplemental hydrogen, the contacting removing at least a portion of the oxygen from the catalyst by a combustion reaction. A molar ratio of hydrocarbon to oxygen in the reactor portion is less than the molar ratio of hydrocarbon to oxygen needed for 50% of the oxygen to react with one or more hydrocarbons present in the reactor portion.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
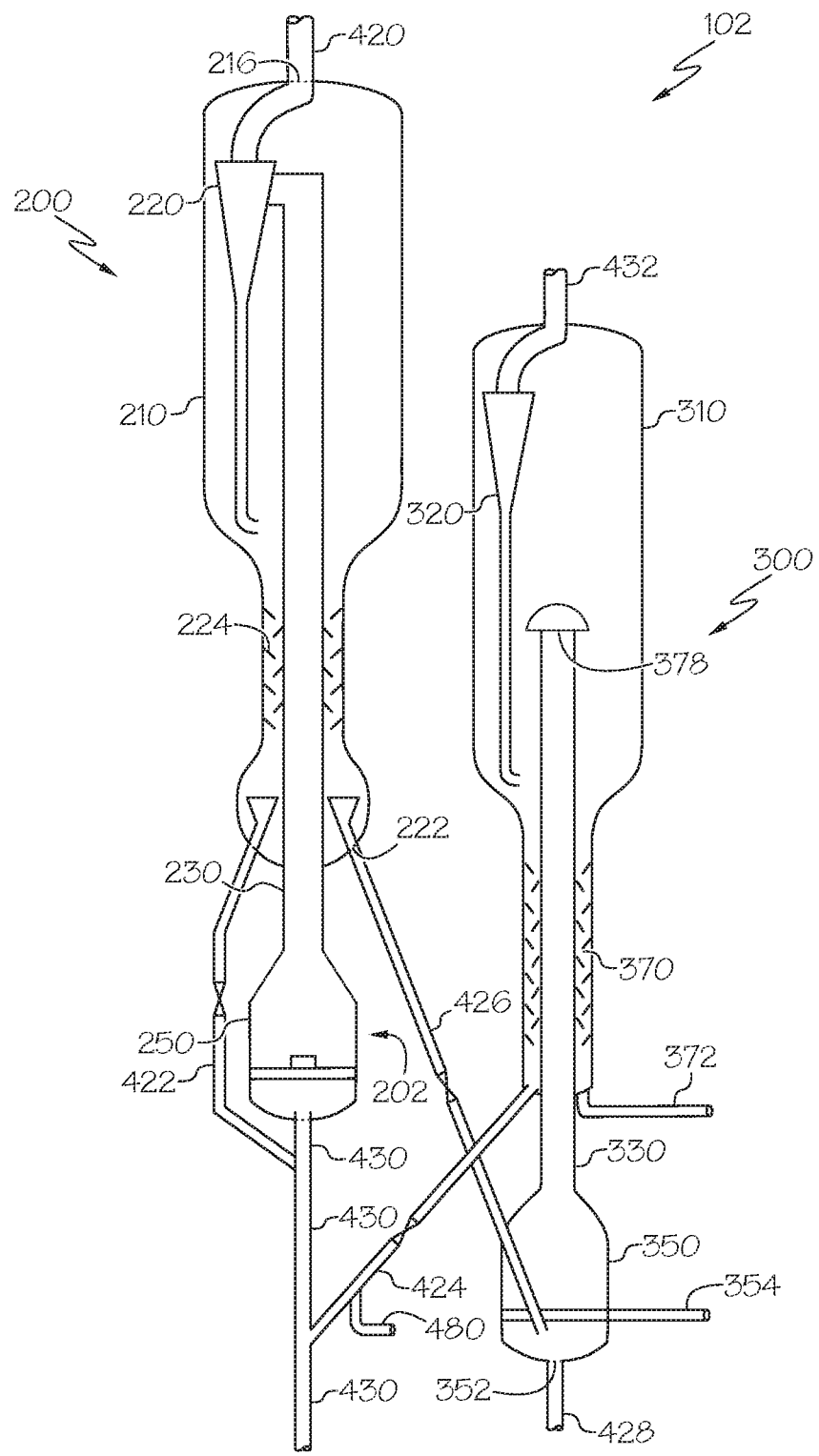
FIG. 1 schematically depicts a reactor system, according to one or more embodiments described herein.

It should be understood that the drawings are schematic in nature, and do not include some components of a reactor system commonly employed in the art, such as, without limitation, temperature transmitters, pressure transmitters, flow meters, pumps, valves, and the like. It would be known that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

The present disclosure is directed to method for operating dehydrogenation processes during non-normal operation. As described herein, non-normal operation may include operation of a dehydrogenation reactor at relatively low reaction temperatures (e.g., temperatures <550° C.). Such low reaction temperature conditions may be present during start-up, shut-down, system recycle event, or unit trip. Non-normal operation may also include periods of operation of a dehydrogenation reactor system in which an inert gas such as nitrogen is circulated through the reactor system to fluidize the catalyst. Circulation of nitrogen in the reactor system may occur during start-up, shutdown, or recycle events, such as interruption in the hydrocarbon feed stream or other condition. When non-normal operation includes circulation of inert gases through the reactor, the temperature of the reactor may be low temperature or high temperature (e.g., >550° C.).

Start-up generally refers to the time when reactor temperature, reactor pressure, flow rates (e.g., flow rates of feed gas to the reactor portion (hydrocarbon and/or inert gases), fuel gas and air for regeneration, gas for stripping and fluidization, oxygen-containing gas for oxygen treating the catalyst, etc.), catalyst recirculation rates, or combinations of these are being established but have not yet reached the desired values for stable operation for the given reaction. Shut-down generally refers to the time when the temperatures, pressures, flow rates, and/or catalyst recirculation rates of the reactor system (i.e., reactor and regenerator) are being reduced prior to the end of the dehydrogenation process reaction.

System recycle (i.e., system recycle) may refer to operation of the reactor system in which the at least a portion of the reactor outlet stream (e.g., product stream) is recycled to the feed or to the reactor portion of the reactor system. System recycle events may include off-spec products events in which the reactor system is operated in a system recycle mode until the product streams and/or operating conditions of the reactor are returned back to target operating conditions. The reactor system may also be operated in system recycle mode in response to planned or unplanned interruptions in operation of other reactor systems, such as a hydrocarbon cracking system, integrated with the reactor system disclosed herein. In some embodiments, system recycle may result in the temperature of the reactor decreasing to a low temperature (i.e., <550° C.). In other circumstances, system recycle may include circulating an inert gas through the reactor to maintain the catalyst in a fluidized state.

Unit trip may refer to conditions when the reactor unit completely shuts down, or conditions in which temperatures are reduced, and/or flow rates of one or more streams are reduced or bypassed due to, for example, runaway conditions during chemical processing. Unit trip may include different levels of unit trips, such as severe unit trips in which the entire reactor system is completely shutdown, or a mid-level trip in which the temperature is reduced, the pressure is reduced, or one or more streams are bypassed. Low-temperature reaction conditions, such as those present during start-up, shut-down, system recycle, or unit trip and conditions in which inert gases are circulated through the reactor system without hydrocarbon feed streams may be referred to as non-normal operating conditions herein. Normal operating conditions refer to high temperature, steady state conditions such as temperatures about 550° C. or those suitable for catalytic reaction of a given reaction. In one or more embodiments, one or more portions of the reactor systems described herein (such as the reactor portion or the combustor) may operate at temperatures of less than or equal to 550° C., 500° C., 450° C., 400° C., 350° C., or even 300° C. during non-normal operating conditions.

Described herein is an example dehydrogenation reactor system which is utilized to provide context for the general hydrogen introduction schemes presently disclosed, which may counteract oxygen buildup. It should be understood that the schematic diagram of FIG. 1 is only an example system, and that other systems suitable for dehydrogenation processing are contemplated herein, and the concepts described herein may be utilized in such alternate systems. For example, the concepts described herein may be equally applied to other systems with alternate reactor units and regeneration units, such as those that operate under non-fluidized conditions or are downers rather than risers. Additionally, the presently described methods and processes for processing a chemical stream in a reactor system should not be limited only to embodiments for reactor systems designed to produce light olefins or alkyl aromatics through fluidized catalytic dehydrogenation, such as the reactor system described with respect to FIG. 1, as other dehydrogenation systems (e.g., utilizing different feedstocks) are contemplated.

As used herein, the term "fluidized reactor system" refers to a reactor system in which one or more reactants are contacted with a catalyst in a fluidization regime, such as bubbling regime, slug flow regime, turbulent regime, fast fluidization regime, pneumatic conveying regime, or combinations thereof in different portions of the system. For example, in a fluidized reactor system, a feed stream containing one or more reactants may be contacted with the circulating catalyst at an operating temperature to conduct a continuous reaction to produce the product stream.

As used herein, "deactivated catalyst" may refer to a catalyst having decreased catalytic activity resulting from buildup of coke and/or loss of catalyst active sites. Catalyst may also exhibit reduced catalytic activity resulting from a reduction in temperature of the catalyst to a temperature less than would generally be needed to achieve the desired reaction rate from the catalyzed reaction. As used herein, "catalytic activity" or "catalyst activity" may refer to the degree to which the catalyst is able to catalyze the reactions conducted in the reactor system. As used herein, "catalyst processing" may refer to preparing the catalyst for re-introduction into the reactor portion of the reactor system and may include removing coke deposits from the catalyst, heating the catalyst, reactivating the catalyst, stripping one or more gases from the catalyst, other processing operations, or any combinations of these. As used herein, "processed catalyst" may refer to catalyst that has been processed in the catalyst processing portion of the reactor system. As used herein, "catalyst reactivation" or "reactivating the catalyst" may refer to processing the deactivated catalyst to restore at least a portion of the catalyst activity to produce a reactivated catalyst. The deactivated catalyst may be reactivated by, but not limited to, recovering catalyst acidity, oxidizing the catalyst, other reactivation process, or combinations thereof. In some embodiments, catalyst reactivation may include treating the catalyst with an oxygen-containing gas at a temperature of greater than or equal to 660° C. for a period of greater than or equal to 2 minutes.

It should be understood that catalytic deactivation and activation, sometimes referred to as deactivation and regeneration, may not occur during non-normal operating conditions. Reference to activation and deactivation, as described herein, is usually in the context of the system operating under normal conditions.

As described herein, "unit trip" which causes reactor cooling may occur due to unexpected situations, such as equipment failure, catalyst issues, or bugs in process automation. Examples include loss of fuel gas, loss of feed due to fouling at feed injection, and high catalyst loss under situations such as cyclone malfunction or high attrition of make-up catalyst. "Shut-down" refers to an intentional shutdown, such as for reactor maintenance. During shutdown or unit trip, both the reactor and regenerator may cool to temperatures at least 100° C. less than that of the normal operation, and may even cool down to ambient temperature. During shut-down or unit trip, fuel gas injection to the regenerator may be either completely stopped or reduced by a significant rate. Consequently, catalyst in the regenerator is not heated to the typical regenerator bed temperatures (e.g., 650° C.-780° C.). During unit trip or shut-down, fresh hydrocarbon injection to the reactor may be stopped and the reactor outlet stream may be recycled back to the feed inlet. During unit trip or shut-down, catalyst when traveling back from regenerator to reactor may further cool down because of additional dehydrogenation reactions or heat loss from the reactor system greatly exceeding the heat addition (zero heat addition with no fuel gas case or small heat addition with reduced fuel gas case). The continuation of such catalyst circulation leads to cooling down of both reactor and catalyst processing portions (e.g. regenerator). During this process, catalyst circulation rate can also be reduced.

As previously discussed, in certain situations, the reactor system may be operated in system recycle in which the reactor outlet stream is recycled back to the reactor. The reactor system may be operated in system recycle mode in response to an off-spec event in which the composition of the reactor outlet stream does not conform to the product stream target standards. In these situations, the reactor outlet stream is recycled back to the reactor while adjustments are made to the system to bring the product composition back into conformance. System recycle may also occur when the reactor system is integrated with another reactor system (e.g., such as a hydrocarbon cracking system) and the other reactor system experiences an interruption (e.g., planned events such as planned maintenance or unplanned events such unexpected failures of equipment such as furnace, compressors, or other equipment). During system recycle operation, fresh feed streams of hydrocarbon and/or hydrogen may be reduced or halted. Recycle of the reactor outlet stream or other stream during such events (an off-spec event or cracker system events) may result in a decrease in the temperature of the reactor below 550° C.

The reactor systems and methods for processing the chemical streams will now be discussed in further detail with reference to FIG. 1. The description, in some instances, relates to normal operating conditions (e.g., temperatures of at least 550° C.) while in other circumstances non-normal operating conditions (e.g., shut-down, start-up, system recycle, or unit trip) are described. The chemical stream that is processed may be referred to as a feed stream, which is processed by a reaction to form a product stream or reactor effluent. The feed stream may comprise a composition, and depending upon the feed stream composition, an appropriate catalyst may be utilized to convert the contents of the feed stream into a product stream that may include light olefins or other chemical products. For example, a feed stream for a fluidized catalytic dehydrogenation (FCDh) reactor system may comprise at least one of propane, n-butane, iso-butane, ethane, or ethylbenzene. In the FCDh system, the feed stream may be converted to light olefins or other products through dehydrogenation in the presence of a dehydrogenation catalyst.

In some embodiments, the catalyst for conducting dehydrogenation in an FCDh reactor system may include a catalyst comprising platinum, gallium, or both. Platinum loading may be from 5-500 ppm by weight and gallium loading may be from 0.25 wt. % to 5 wt. %. In some embodiments, the catalyst may further include one or more other noble metals from Groups 9 and 10 of the IUPAC periodic table. For example, in some embodiments, the catalyst may include one or more noble metals chosen from, palladium (Pd), rhenium (Rh), iridium (Jr), or combinations of these. In some embodiments, the catalyst may also include one or more metals chosen from indium (In), germanium (Ge), or combinations of these. The catalyst may also include a promoter metal, such as an alkali metal or an alkaline metal. In some embodiments, the promoter metal may be potassium (such as from 0-2 wt. % of the catalyst). The metals of the catalyst may be supported on a carrier. The carrier may include one or more inorganic bulk metal oxides, such as silica, alumina, silica-containing alumina, zirconia ($ZrO_2$), titania ($TiO_2$), other metal oxides, or combinations of metal oxides. In some embodiments, the carrier may include a microporous material, such as ZSM-5 zeolite. The catalytic metals, such as platinum, gallium, potassium, and/or other catalytically active metals, may be supported on the surface of the carrier or incorporated into the carrier. In some embodiments, the catalyst may include platinum, gallium, and optionally potassium supported on a silica-containing alumina carrier. In additional embodiments, the support may comprise chromium, such as $Cr_2O_3$ in an amount of from 6 wt. % to 30 wt. % of the catalyst (such as from 13 wt. % to 25 wt. %).

Referring now to FIG. 1, an example reactor system 102 is schematically depicted. The reactor system 102 generally includes a reactor portion 200 and a catalyst processing portion 300. As used herein in the context of FIG. 1, the reactor portion 200 refers to the portion of a reactor system 102 in which the major process reaction takes place. For example, the reactor system 102 may be an FCDh system in which the feed stream is dehydrogenated in the presence of the dehydrogenation catalyst in the reactor portion 200 of the reactor system 102. The reactor portion 200 comprises a reactor 202 which may include a downstream reactor section 230, an upstream reactor section 250, and a catalyst separation section 210, which serves to separate the catalyst from the chemical products formed in the reactor 202.

Also, as used herein, the catalyst processing portion 300 of the system of FIG. 1 generally refers to the portion of a reactor system 102 in which the catalyst is in some way processed, such as removal of coke deposits, heating of the catalyst, reactivating the catalyst, other processing operations, or combinations of these, during normal operation. In some embodiments, the catalyst processing portion 300 may include a combustor 350, a riser 330, a catalyst separation section 310, and an oxygen treatment zone 370. The combustor 350 of the catalyst processing portion 300 may include one or more lower combustor inlet ports 352 and may be in fluid communication with the riser 330. The combustor 350 may be in fluid communication with the catalyst separation section 210 via standpipe 426, which may supply deactivated catalyst (during normal operating conditions) from the reactor portion 200 to the catalyst processing portion 300 for catalyst processing (e.g., coke removal, heating, reactivating, etc.). The oxygen treatment zone 370 may be in fluid communication with the upstream reactor section 250 (e.g., via standpipe 424 and transport riser 430), which may supply processed catalyst from the catalyst processing portion 300 back to the reactor portion 200. The combustor 350 may include the lower combustor inlet port 352 where air inlet 428 connects to the combustor 350. The air inlet 428 may supply air or other reactive gases, such as an oxygen-containing gas to the combustor 350. Air and/or other reactive gases, may be introduced to the combustor 350 to aid in combustion of the supplemental fuel. The combustor 350 may also include a fuel inlet 354. The fuel inlet 354 may supply a fuel, such as a hydrocarbon stream 356 to the combustor 350. The oxygen treatment zone 370 may include an oxygen-containing gas inlet 372, which may supply an oxygen-containing gas to the oxygen treatment zone 370 for oxygen treatment of the catalyst.

Referring to FIG. 1, general operation of the reactor system 102 to conduct a continuous reaction under normal operating conditions will be described. During operation of the reactor portion 200 of the reactor system 102, the feed stream may enter the transport riser 430, and the product stream may exit the reactor system 102 via pipe 420. According to one or more embodiments, the reactor system 102 may be operated by feeding a chemical feed (e.g., in a feed stream) and a fluidized catalyst into the upstream reactor section 250. The chemical feed may contact the catalyst in the upstream reactor section 250, and each may flow upwardly into and through the downstream reactor section 230 to produce a chemical product under normal operating conditions. When the catalyst carrying free oxygen is transported to the reactor portion 200, the free oxygen carried by the catalyst into the reactor portion 200 may combust with hydrocarbons streams (feed, products etc) in the reactor portion 200 to form oxygen containing compounds. Thus, free oxygen in the reactor portion 200 may be consumed by reaction. However, at the lower temperatures during non-normal operating conditions, the free oxygen carried by the catalyst may not be able to react with hydrocarbons in the reactor portion 200 and, thus, may stay in the FCDh product stream. Additionally, when inert gases, such as nitrogen, is circulated through the reactor system instead of the hydrocarbon feedstream, regardless of the temperature, the free oxygen carried by the catalyst or released therefrom may have no hydrocarbons to react with and may, therefore, buildup in the FCDh product stream.

The chemical product and the catalyst may be passed out of the downstream reactor section 230 to a separation device 220 in the catalyst separation section 210. The catalyst may be separated from the chemical product in the separation device 220. The chemical product may then be transported out of the catalyst separation section 210. For example, the separated vapors may be removed from the reactor system 102 via a pipe 420 at a gas outlet port 216 of the catalyst separation section 210. According to one or more embodiments, the separation device 220 may be a cyclonic separation system, which may include two or more stages of cyclonic separation.

According to some embodiments, following separation from vapors in the separation device 220, the catalyst may generally move through the stripper 224 to the reactor catalyst outlet port 222 where the catalyst may be transferred out of the reactor portion 200 via standpipe 426 and into the catalyst processing portion 300. Optionally, the catalyst may also be transferred directly back into the upstream reactor section 250 via standpipe 422. In some embodiments, recycled catalyst from the stripper 224 may be premixed with processed catalyst from the catalyst processing portion 300 in the transport riser 430.

The separated catalyst may be passed from the catalyst separation section 210 to the combustor 350 of the catalyst processing portion 300. The catalyst may be processed in the catalyst processing portion 300 during normal operation to remove coke deposits, heat the catalyst, reactivate the catalyst, other catalyst processing, or any combinations of these. As previously discussed, processing the catalyst in the catalyst processing portion 300 may include removing coke deposits from the catalyst, raising the temperature of the catalyst through combustion of a combustion fuel source, reactivating the catalyst, stripping one or more constituents from the catalyst, other processing operation, or combinations of these. In some embodiments, processing the catalyst in the processing portion 300 may include combusting a combustion fuel source in the presence of the catalyst in the combustor 350 to remove coke deposits and/or heat the catalyst to produce a heated catalyst. The heated catalyst may be separated from the combustion gases in the catalyst separation portion 310. In some embodiments under normal system operation, the heated catalyst may then be reactivated by conducting an oxygen treatment of the heated catalyst. The oxygen treatment may include exposing the catalyst to an oxygen-containing gas for a period of time sufficient to reactivate the catalyst.

In some embodiments, the combustion fuel source may include coke or other contaminants deposited on the catalyst in the reactor portion 200 of the reactor system 102. In some reaction systems, the catalyst may be coked following the reactions in the reactor portion 200, and the coke may be removed from the catalyst by a combustion reaction in the combustor 350. For example, oxidizer (such as air) may be fed into the combustor 350 via the air inlet 428.

Referring to FIG. 1, the processed catalyst may be passed out of the combustor 350 and through the riser 330 to a riser termination separator 378, where the gas and solid components from the riser 330 may be at least partially separated. The vapor and remaining solids may be transported to a secondary separation device 320 in the catalyst separation section 310 where the remaining processed catalyst is separated from the gases from the catalyst processing (e.g., gases emitted by combustion of coke deposits and supplemental fuel). In some embodiments, the secondary separation device 320 may include one or a plurality of cyclone separation units, which may be arranged in series or in multiple cyclone pairs. The combustion gases from combustion of coke and/or the supplemental fuel during processing of the catalyst or other gases introduced to the catalyst during catalyst processing may be removed from the catalyst processing portion 300 via a combustion gas outlet 432.

As previously discussed, processing the catalyst in the catalyst processing portion 300 of the reactor system 102 may include reactivating the catalyst when the system operates under normal conditions. Combustion of the supplemental fuel in the presence of the catalyst to heat the catalyst may further deactivate the catalyst. Thus, in some embodiments during normal operating conditions, the catalyst may be reactivated by conditioning the catalyst through an oxygen treatment. The oxygen treatment to reactivate the catalyst may be conducted after combustion of the supplemental fuel to heat the catalyst. The oxygen treatment may include treating the heated catalyst with an oxygen-containing gas for a period of at least two minutes, which may reactivate the catalyst to produce a reactivated catalyst. The oxygen-containing gas may include an oxygen content of from 5 mole % to 100 mole % based on total molar flow rate of the oxygen-containing gas. In some embodiments, the catalyst may be reactivated by conditioning the catalyst through an oxygen treatment. Oxygen treatment of the catalyst may include maintaining the catalyst at a temperature of at least 660° C. while exposing the catalyst to a flow of an oxygen-containing gas for a period of time greater than two minutes and sufficient to produce a reactivated catalyst having a catalytic activity that is greater than the heated catalyst after being heated by combustion of the supplemental fuel.

Referring to FIG. 1, treatment of the heated catalyst with the oxygen-containing gas may be conducted in the oxygen treatment zone 370. In some embodiments, the oxygen treatment zone 370 may be downstream of the catalyst separation portion 310 of the catalyst processing portion 300, such that the heated catalyst is separated from the combustion gases before being exposed to the oxygen-containing gas during the oxygen treatment. In some embodiments, the oxygen treatment zone 370 may include a fluid solids contacting device. The fluid solids contacting device may include baffles or grid structures to facilitate contact of the heated catalyst with the oxygen-containing gas. Examples of fluid solid contacting devices are described in further detail in U.S. Pat. Nos. 9,827,543 and 9,815,040, both of which are incorporated by reference herein in their entirety.

In some embodiments, processing the catalyst in the catalyst processing portion 300 of the reactor system 102 under normal conditions may further include stripping the oxygen-containing reactivated catalyst of molecular oxygen trapped within or between catalyst particles and physisorbed oxygen that is desorbable at a temperature of at least 660° C. The stripping step may include maintaining the oxygen-containing reactivated catalyst at a temperature of at least 660° C. and exposing the oxygen-containing reactivated catalyst to a stripping gas that is substantially free of molecular oxygen and combustible fuels for a period of time to remove the molecular oxygen from between particles and physisorbed oxygen that is desorbable at the temperature of at least 660° C. Further description of these catalyst reactivation processes are disclosed in U.S. Pat. No. 9,834,496, which is incorporated by reference in the present disclosure in its entirety.

While catalyst reactivation generally occurs during normal system conditions, under low temperature conditions, such as during non-normal operating conditions described herein, the catalyst may not be reactivated in the catalyst processing portion. For example, the catalyst may not be heated to a sufficient amount to be active for dehydrogenation reactions, or may still contain coke deposits since insufficient combustion of the coke may take place during low temperature conditions in the combustor 350, such as during shut-down, start-up, system recycle, or unit trip. However, even as the catalyst may not be considered activated following processing during the non-normal operating conditions, the catalyst following processing (e.g., in the standpipe 424) may carry oxygen over into the reactor portion 200. For example, the catalyst may carry from 0.001 wt. % to 0.1 wt. % of oxygen. It should be understood that when described herein, oxygen carried by the catalyst may include oxygen trapped inside the pore structures of catalyst (intra-particle) or oxygen trapped between the catalyst particles (inter-particle). The oxygen carried by the catalyst is exclusive of oxygen atoms which are chemically bonded to the catalyst, such as metal oxides used as support materials, etc. Thus, this oxygen is sometimes referred to herein as "free oxygen" since it may be carried by the catalyst but is not chemically bonded to the catalyst. This free oxygen described herein may be accumulated on the catalyst from the exposure of the catalyst to oxygen containing gas in the combustor 350 and/or the oxygen treatment zone 370.

Following processing of the catalyst, the processed catalyst may be passed from the catalyst processing portion 300 back into the reactor portion 200 via standpipe 424. For example, in some embodiments, the processed catalyst may be passed from the oxygen treatment zone 370 of the catalyst processing portion 300 to the upstream reactor section 250 via standpipe 424 and transport riser 430, where the processed catalyst may be further utilized in a catalytic reaction. Thus, in operation, the catalyst may cycle between the reactor portion 200 and the catalyst processing portion 300. In general, the processed chemical streams, including the feed streams and product streams may be gaseous, and the catalyst may be a fluidized particulate solid.

As was explained herein, under normal operating temperatures, some or all of the free oxygen carried by the catalyst from processing portion 300 to reactor 200 may be reacted with a hydrocarbon, such as the feed, product, or both, to form oxygen-containing compounds. Thus, in high temperature environments, such as greater than 550° C., free oxygen from the catalyst may be substantially eliminated from the product stream. However, under lower temperature conditions during non-normal operating conditions, such as during start-up, shut-down, system recycle, or unit trip, the free oxygen carried by the catalyst may not be reacted with the hydrocarbons normally present in the reactor 200, causing the free oxygen to be present in the product stream. Additionally, under high temperature conditions in which inert gases are circulated through the reactor system, hydrocarbons may not be present to react with the free oxygen carried by the catalyst or released therefrom, causing the free oxygen to be present in the product stream. Presence of such free oxygen in the product stream may be undesirable for a number or reasons discussed herein.

In some embodiments, the temperature in the reactor portion 200 may be less than needed for at least 50% (or at least 25%, or at least 15%, or at least 10%, or even at least 5%) of the free oxygen to react with one or more hydrocarbons present in the reactor portion 200. Temperatures which may correspond with these conditions may include less than 550° C., less than 500° C., less than 450° C., less than 400° C., less than 350° C., or even less than 300° C. In other embodiments, a molar ratio of hydrocarbons to free oxygen in the reactor portion 200 may be less than a molar ratio of hydrocarbons to free oxygen at which at least 50% (or at least 25%, or at least 15%, or at least 10%, or even at least 5%) of the free oxygen reacts with the one or more hydrocarbons. In some embodiments, the molar ratio of hydrocarbon to free oxygen in the reactor portion 200 may be less than or equal to 0.05:1, less than or equal to 0.1:1, less than or equal to 0.25:1, less than or equal to 0.5:1, or even less than or equal to 1:1.

In one or more embodiments, the reactor system 102 may include a hydrogen inlet stream 480 which provides supplemental hydrogen to the reactor system 102. The supplemental hydrogen of stream 480 may generally contact the catalyst which contains free oxygen or may contact the free oxygen released/stripped from the catalyst by hydrocarbons on the catalyst. In one or more embodiments, the hydrogen contacts the free oxygen carried by the catalyst to the reactor or released from the catalyst anywhere in the reactor system 102 between the catalyst processing portion 300 and the separation of the catalyst from the reactor effluent (e.g., at the separation device 220). For example, hydrogen inlet stream 480 may contact the catalyst at standpipe 424, as shown in FIG. 1. In these embodiments, the supplemental hydrogen may contact the free oxygen carried by the catalyst and may react with the free oxygen by combustion. In other embodiments, the supplemental hydrogen may enter the reactor system 102 at transport riser 430 (either above or below the connection with the standpipe 424), or even be injected directly into the reactor 202. In some embodiments in which the supplemental hydrogen enters the reactor downstream of standpipe 424, the free oxygen carried by the catalyst may be released/stripped from the catalyst by the hydrocarbons from the catalyst, thereby releasing the free oxygen into the gas phase where the free oxygen may contact and react with the supplemental hydrogen. This combustion reaction with hydrogen may take place at lower temperatures than would be present during normal operating conditions. For example, the hydrogen combustion may take place at temperatures at or below 550° C.

It should be understood that the "supplemental hydrogen" described herein is distinct from any hydrogen that may be formed by dehydrogenation of the feed materials. Such supplemental hydrogen is not formed in situ in the reactor 102 and instantaneously reacted with the present oxygen. That is, under normal operating conditions, hydrogen may be formed in the reactor 202 by dehydrogenation. However, under lower temperature conditions, such hydrogen may not be produced at all or may not be produced in quantities sufficient to react with the free oxygen carried by the catalyst to the reactor to remove the free oxygen to a desired amount. In one or more embodiments, temperature of the reactor portion 200 is not sufficient to produce even half of a molar equivalent of hydrogen relative to the amount of free oxygen carried by the catalyst. In some embodiments, hydrocarbons may not be present to react with the catalyst to produce hydrogen, regardless of the temperature of the reactor, such as when inert gases are circulated through the reactor.

In order to fully combust the free oxygen, hydrogen needs to be produced in at least an amount resulting in a molar ratio of hydrogen to free oxygen of 2:1. In some embodiments, at least 0.5 moles supplemental hydrogen may be introduced to the reactor system 102 for each mole of free oxygen, or even 1 to 2 moles of supplemental hydrogen for each mole of free oxygen carried by the catalyst. At low temperature conditions, that amount of hydrogen may not be produced by dehydrogenation in the reactor 202.

It has been discovered that hydrogen may be particularly useful as a combustion reactant with oxygen at the relatively low temperature conditions during non-normal operating conditions, such as at start-up, shut-down, system recycle, or unit trip. For example, many combustible fuels may require relatively high temperatures for sufficient combustions. Temperatures during non-normal conditions may be too low for combustion of fuels such as methane, ethane, ethylene, propane, propylene, and coke. These fuels may not be utilized in the present embodiments.

A person skilled in the art may appreciate that some gallium-based catalysts, such as those described in context of the system of FIG. 1, may be deactivated by exposure to hydrogen. Therefore, under normal conditions, it may not be desirable to contact such a catalyst with hydrogen. However, it has unexpectedly been discovered that in some cases, such as in non-normal operating conditions resulting in low temperatures, that hydrogen may be a suitable material for contact with the catalyst during non-production periods to eliminate free oxygen carried by the catalyst.

The supplemental hydrogen may be present in the form of any stream containing hydrogen. Contemplated streams that be utilized in the hydrogen inlet stream 480 include, without limitation, high purity hydrogen, hydrogen mixed with steam, hydrogen mixed with nitrogen, hydrogen mixed with hydrocarbons, or any mixture of these. In one or more embodiments, hydrogen may make up at least about 5 mol. %, at least 10 mol. %, at least 25 mol. %, even at least 50 mol. %, or even at least 95 mol. % of the stream entering through the hydrogen inlet stream 480.

Figure 2:
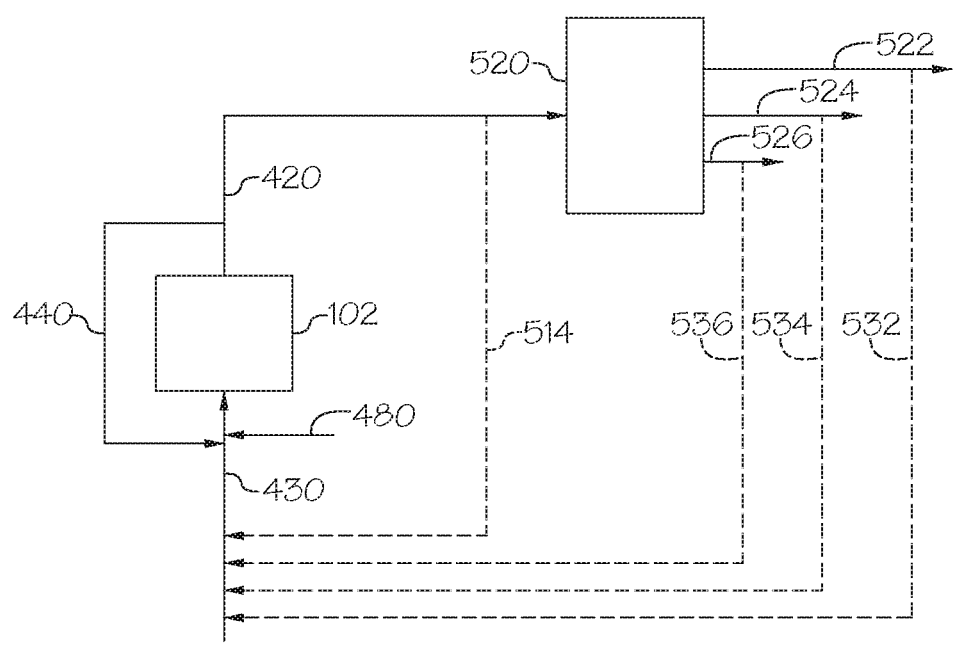
FIG. 2 schematically depicts the reactor system of FIG. 1 as a stand-alone reactor system operating in system recycle, according to one or more embodiments shown and described herein.

Referring to FIG. 2, the reactor system 102 is shown with an outlet stream processing portion 520 downstream of the reactor system 102. The outlet stream processing portion 520 may separate the reactor outlet stream into a propane stream 522, a propylene stream 524, an off-gas stream 526, or other streams (not shown). FIG. 2 schematically depicts operation of the reactor system 102 in a system recycle mode. As shown in FIG. 2, the reactor outlet stream may be recycled from the pipe 420 back to the transport riser 430 by way of recycle pipe 440 during system recycle operation of the reactor system 102. For operation of the reactor system 102 in system recycle mode at temperatures less than 550° C., oxygen may continue to buildup in the reactor system 102 if not consumed. For example, free oxygen in the reactor outlet stream may be recycled back to the reactor portion 200 through recycle pipe 440. Additionally, the circulating catalyst may continue to carry free oxygen from the catalyst processing portion 300 to the reactor portion 200 of the reactor system 102. If the free oxygen is not consumed within the reactor system 102 during non-normal operation at low temperatures, buildup of the free oxygen can occur, which can lead to a high risk of explosion. During system recycle in which the reactor system 102 is at lower temperature (i.e., <550° C.), the supplemental hydrogen may be introduced through hydrogen inlet 480. As previously discussed, the supplemental hydrogen may enable the free-oxygen to be consumed in the reactor portion 200 to prevent or reduce buildup of free-oxygen in the reactor system 102 during system recycle. Although the recycle pipe 440 and hydrogen inlet 480 are shown in FIG. 2 as connecting to the transport riser 430, it is understood that the recycle pipe 440 and/or the hydrogen inlet 480 may introduce the recycled reactor outlet stream and supplemental hydrogen, respectively, directly to the reactor portion 200 (FIG. 1).

Alternatively or additionally, in some embodiments, at least one of the propane stream 522, propylene stream 524, off-gas stream 526, or combinations of these streams may be recycled back to the transport riser 430 and/or the reactor portion 200 (FIG. 1) of the reactor system 102. For example, during system recycle operation, the propane stream 522 may be recycled back to the transport riser 430 and/or reactor portion 200 through propane recycle 532. In some embodiments, the propylene stream 524 may be recycled back to the transport riser 430 and/or reactor portion 200 through propylene recycle 534. Also, in some embodiments, off-gas 526 may be recycled back to the transport riser 430 and/or reactor portion 200 through off-gas recycle 536. In some embodiments, the outlet stream processing portion 520 may include a multi-stage crack gas compressor (CGC) and any of the intermediate streams between stages of the CGC may be recycled back to the transport riser 430 and/or the reactor portion 200 of the reactor system 102. In some embodiments, the hydrocarbon feed stream may be halted and replaced with an inert gas stream, such as nitrogen, which may be recycled through recycle pipe 440. Thus, the system recycle operation may be conducted with an inert gas, which may be generally free of hydrocarbons.

Figure 3:
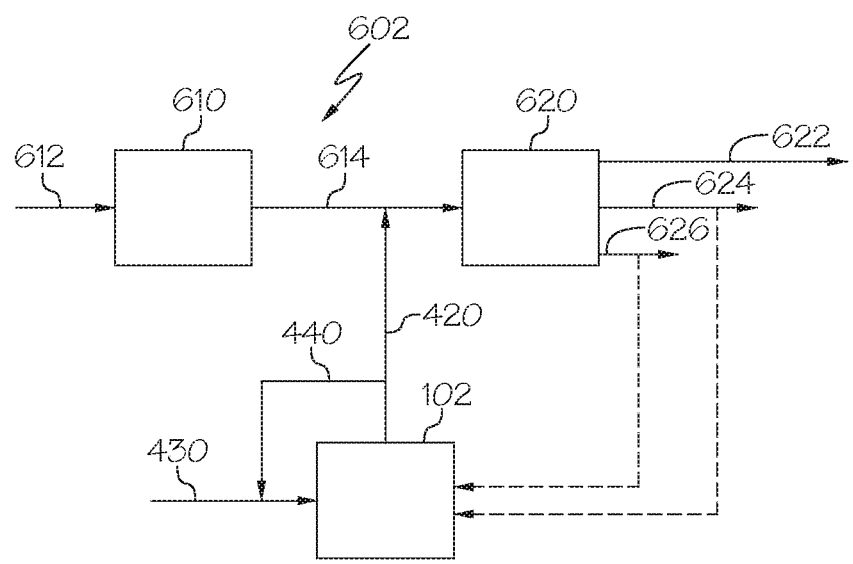
FIG. 3 schematically depicts the reactor system of FIG. 1 integrated with a cracking unit, according to one or more embodiments described herein.

Referring to FIG. 3, the reactor system 102 may be integrated with a hydrocarbon cracking process 602. The light hydrocarbon cracking process 602 may include a light hydrocarbon cracking unit 610 and a light hydrocarbon processing portion 620. During continuous operation of the light hydrocarbon cracking process 602, one or a plurality of light hydrocarbon streams 612 may be introduced to the light hydrocarbon cracking unit 610, in which light hydrocarbons in the hydrocarbon streams 612 are cracked to produce a cracker effluent 614 that includes one or more reaction products. For example, in some embodiments, the light hydrocarbon cracking unit 610 may be a steam cracker and the light hydrocarbon streams 612 may include ethane and propane, which may be steam cracked in the steam cracker to produce at least ethylene. The cracker effluent 614 may be passed to the light hydrocarbon processing portion 620 of the light hydrocarbon cracking process 602. The light hydrocarbon processing portion 620 may include a plurality of unit operations, such as but not limited to acetylene conversion, vapor compression, separation, sulfur and carbon dioxide removal, drying, or other operations. The light hydrocarbon processing portion 620 may ultimately separate the cracker effluent 614 into a plurality of gaseous streams, such as but not limited to, an ethylene product stream 622, a propylene product stream 624, a propane stream 626, and other streams.

The cracker effluent may include acetylene, which may be converted by the hydrocarbon processing portion 620 through hydrogenation. As is described in "Overview on C2 and C3 Selective Hydrogenation in Ethylene Plants" by Edgar L. Mohundro, $15^{th}$ Ethylene Produces Conference, 2003 AICHE Spring National Meeting, New Orleans, La., the contents of which are incorporated herein, several configurations of selective acetylene hydrogenation may be utilized. These include "front-end" and "back end" configurations. Oxygen present in the acetylene hydrogenation reactor may cause problems, such as run-away reactions. Even amounts of oxygen as low as 50 ppmv for 5 min. may cause hot spots which trigger run-away and damage the catalyst which may require shut-down of the acetylene hydrogenation reactor.

In one or more embodiments, as shown in FIG. 3, the product effluent of the reactor system 102 may be combined with the cracker effluent 614, which enters the light hydrocarbon processing portion. Oxygen contained in the effluent of the reactor system 102 may cause problems in the acetylene hydrogenation reaction, as described herein. The methods described herein may limit the amount of oxygen entering the acetylene hydrogenation reactor.

As shown in FIG. 3, the reactor system 102 integrated with the hydrocarbon cracking process 602 may also be operated in system recycle mode during off-spec events or other situations. In system recycle mode, the reactor outlet stream from the reactor system 102 may be recycled back to the transport riser 430 or the reactor portion 200 of the reactor system 102 by way of recycle pipe 440. The reactor outlet stream may be recycled from a point downstream of a booster compressor (not shown) disposed in pipe 420. Alternatively or additionally, any of the propylene stream 624, propane stream 626, other stream, or combinations of these streams recovered from the light hydrocarbon processing portion 620 may be recycled back to the transport riser 430 and/or the reactor portion 200 of the reactor system 102. Further, the light hydrocarbon processing portion 620 may also include a CGC and any of the intermediate streams between stages of the CGC may be recycled back to the transport riser 430 and/or the reactor portion 200 of the reactor system 102.

The reactor system 102 integrated with the hydrocarbon cracking process 602 may also experience buildup of free oxygen in the reactor system 102 when operated in system recycle mode, resulting in increased risk of explosion. For example, recycling the reactor outlet stream from pipe 424 back to the reactor may also recycle any free oxygen in the reactor outlet stream back to the reactor. Additionally, the circulating catalyst may continue to carry free oxygen from the catalyst processing portion 300 of the reactor system 102 to the reactor portion 200. In some embodiments, the hydrocarbon feed stream may be halted and replaced with an inert gas stream, such as nitrogen, which may be recycled through recycle pipe 440. Thus, the system recycle operation may be conducted with an inert gas, which may be generally free of hydrocarbons.

EXAMPLES

Embodiments of the present disclosure will be further clarified by the following examples, which should not be construed as limiting on the disclosed and/or claimed embodiments presently described.

Example 1

Figure 4:
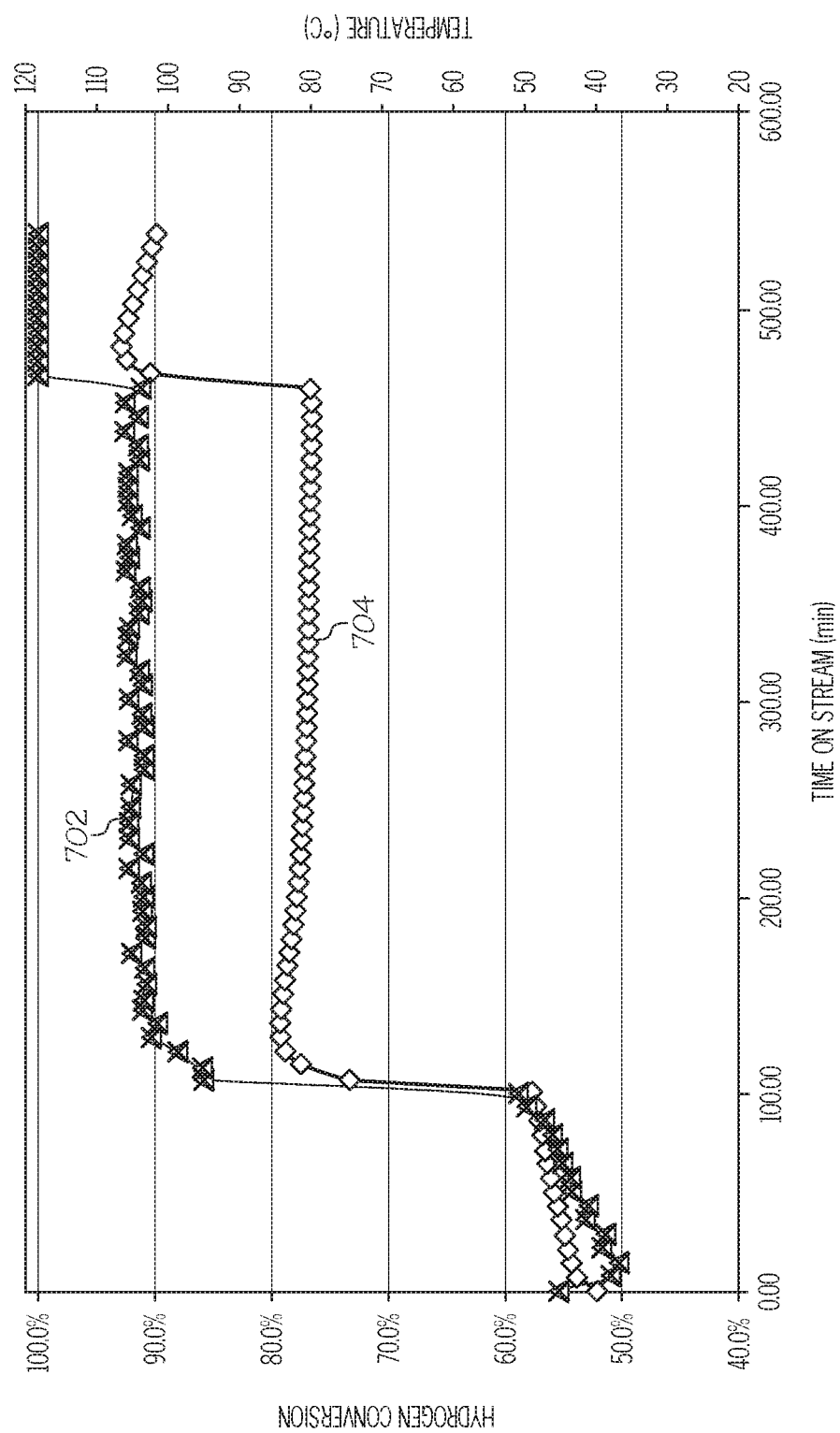
FIG. 4 graphically depicts hydrogen combustion with oxygen in the presence of a catalyst containing platinum, according to one or more embodiments described herein.

FIG. 4 graphically depicts the conversion 702 of a commencement fuel gas stream of hydrogen (y-axis—left) and the temperature 704 (y-axis—right) as functions of time-on-stream (TOS) (x-axis) for combustion of hydrogen in the presence of a gallium catalyst with a platinum promoter. The experiment was carried out in a bubbling bed testing rig with a 1" diameter quartz tube reactor. The reactor was loaded with 50 grams catalyst. The inlet gas was introduced at the bottom of the reactor and a quartz frit was used to distribute the gas flow across the reactor diameter. The volumetric flow of the inlet gas was 1690 standard cubic centimeters per minute. The inlet gas flow caused the catalyst to fluidize. The inlet gas composition was 6.2% O2, 1.0% He, 2.0% H2 and the balance nitrogen. The temperature of the system was increased from 50° C. to about 80° C. after 100 minutes on stream and further increased to over 100° C. at 450 minutes on stream. As shown in FIG. 4, the conversion of hydrogen may be greater than 50% at temperatures between 35° C. and 50° C. At temperatures of about 80° C., the conversion of hydrogen may be greater than 90%. Above 100° C. the conversion of hydrogen may be about 100%.

Example 2

For comparative purposes, $CH_4$ combustion was carried out in the same bubbling bed testing rig as described in Example 1 with 50 grams of the same gallium catalyst with platinum promoter of Example 1. The volumetric flow of the inlet gas was maintained at 1690 standard cubic centimeters per minute, while the inlet gas composition changed to 6.2% O2, 1.0% He, 2.0% methane and the balance nitrogen. The combustion of methane with oxygen was measured between 300 and 600° C. and at a pressure of 2 psig. The results are reported below in Table 1. The percentage of methane converted at temperatures less than 550° C. is very low. Only 3.1% conversion was obtained at 550° C. under the testing conditions.

In view of these experimental results, hydrogen is a desirable combustion fuel when temperatures are relatively low, such as in the embodiments presently described.

TABLE 1

| CH4 conversion at low temperatures | |
|---|---|
| Temperature, ° C. | $CH_4$ Conv., mol. % |
| 300 | 0.0% |
| 350 | 0.0% |
| 400 | 0.1% |
| 450 | 0.3% |
| 500 | 1.0% |
| 550 | 3.1% |

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

Generally, "inlet ports" and "outlet ports" of any system unit of the reactor system 102 described herein refer to openings, holes, channels, apertures, gaps, or other like mechanical features in the system unit. For example, inlet ports allow for the entrance of materials to the particular system unit and outlet ports allow for the exit of materials from the particular system unit. Generally, an outlet port or inlet port will define the area of a system unit of the reactor system 102 to which a pipe, conduit, tube, hose, material transport line, or like mechanical feature is attached, or to a portion of the system unit to which another system unit is directly attached. While inlet ports and outlet ports may sometimes be described herein functionally in operation, they may have similar or identical physical characteristics, and their respective functions in an operational system should not be construed as limiting on their physical structures.

It will be apparent to those skilled in the art that various modifications and variations can be made to the present invention without departing from the spirit and scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

The invention claimed is:

1. A method for operating a dehydrogenation process, the method comprising:
   contacting a feed stream with a catalyst in a reactor portion of a reactor system to form a reactor effluent stream, wherein the temperature or the molar ratio of hydrocarbon to oxygen in the reactor portion is less than a temperature or molar ratio of hydrocarbon to oxygen needed for 50% of the oxygen to react with one or more hydrocarbons present in the reactor portion;
   separating at least a portion of the reactor effluent stream from the catalyst;
   passing the catalyst to a catalyst processing portion and processing the catalyst, wherein processing the catalyst comprises contacting the catalyst with an oxygen-containing gas;

passing the catalyst from the processing portion to the reactor portion, wherein the catalyst exiting the processing portion comprises at least 0.001 wt. % oxygen; and contacting the catalyst with supplemental hydrogen, the contacting removing at least a portion of the oxygen from the catalyst by a combustion reaction.

2. The method of claim 1, wherein the temperature in the reactor portion is less than 550° C.

3. The method of claim 1, wherein the dehydrogenation process is operating during start-up.

4. The method of claim 1, wherein the dehydrogenation process is operating during shut-down.

5. The method of claim 1, wherein the dehydrogenation process is operating during unit trip.

6. The method of claim 1, wherein the dehydrogenation process is operating in system recycle.

7. The method of claim 1, wherein the temperature of the reactor portion is not sufficient to produce half of the molar equivalent of hydrogen with respect to the oxygen of the catalyst.

8. The method of claim 1, wherein the contacting of the supplemental hydrogen with the catalyst occurs downstream of the catalyst processing portion and upstream of a separator where the separating at least a portion of the reactor effluent from the catalyst is conducted.

9. The method of claim 1, wherein the catalyst comprises platinum, gallium, or both.

10. The method of claim 1, wherein the reactor effluent stream is combined with the effluent of a steam cracker to form a mixed stream.

11. The method of claim 10, wherein the mixed stream comprises acetylene, and the acetylene is hydrogenated.

12. The method of claim 1, wherein the feed stream consists of an inert gas and contacting the feed stream with the catalyst in the reactor portion comprises circulating the inert gas through the reactor system to fluidize the catalyst in the reactor portion.

13. A method for operating a dehydrogenation process, the method comprising:

contacting a feed stream with a catalyst in a reactor portion of a reactor system to form a reactor effluent stream, wherein the temperature in the reactor portion is less than 550° C.;

separating at least a portion of the reactor effluent stream from the catalyst;

passing the catalyst to a catalyst processing portion and processing the catalyst, wherein processing the catalyst comprises contacting the catalyst with an oxygen-containing gas;

passing the catalyst from the processing portion to the reactor portion, wherein the catalyst exiting the processing portion comprises at least 0.001 wt. % oxygen; and contacting the catalyst with supplemental hydrogen, the contacting removing at least a portion of the oxygen from the catalyst by a combustion reaction.

14. The method of claim 13, wherein the reactor effluent stream is combined with the effluent of a steam cracker to form a mixed stream.

15. The method of claim 13, wherein the temperature of the reactor portion is not sufficient to produce half of the molar equivalent of hydrogen with respect to the oxygen of the catalyst.

16. The method of claim 13, wherein the contacting of the supplemental hydrogen with the catalyst occurs downstream of the catalyst processing portion and upstream of a separator where the separating at least a portion of the reactor effluent from the catalyst is conducted.

17. The method of claim 13, wherein the feed stream consists of an inert gas and contacting the feed stream with the catalyst in the reactor portion comprises circulating the inert gas through the reactor system to fluidize the catalyst in the reactor portion.

18. A method for operating a dehydrogenation process, the method comprising:

circulating an inert gas through a reactor system to fluidize a catalyst in a reactor portion of the reactor system, wherein the temperature or the molar ratio of hydrocarbon to oxygen in the reactor portion is less than a temperature or molar ratio of hydrocarbon to oxygen needed for 50% of the oxygen to react with one or more hydrocarbons present in the reactor portion;

separating at least a portion of the inert gas from the catalyst;

passing the catalyst to a catalyst processing portion and processing the catalyst, wherein processing the catalyst comprises contacting the catalyst with an oxygen-containing gas;

passing the catalyst from the processing portion to the reactor portion, wherein the catalyst exiting the processing portion comprises at least 0.001 wt. % oxygen; and contacting the catalyst with supplemental hydrogen, the contacting removing at least a portion of the oxygen from the catalyst by a combustion reaction.

\* \* \* \* \*